United States Patent
Yencho et al.

(10) Patent No.: US 6,913,609 B2
(45) Date of Patent: Jul. 5, 2005

(54) ACCESS PORT SYSTEM FOR ANASTOMOSIS

(75) Inventors: Stephen A. Yencho, Menlo Park, CA (US); Bernard A. Hausen, Menlo Park, CA (US); Jaime S. Vargas, Menlo Park, CA (US)

(73) Assignee: Cardica, Inc., Redwood City, CA (US)

(*) Notice: Subject to any disclaimer, the term of this patent is extended or adjusted under 35 U.S.C. 154(b) by 385 days.

(21) Appl. No.: 09/967,684

(22) Filed: Sep. 28, 2001

(65) Prior Publication Data

US 2003/0065343 A1 Apr. 3, 2003

(51) Int. Cl.[7] ............................................. A61B 17/08
(52) U.S. Cl. ................................. 606/153; 604/167.01
(58) Field of Search .......................... 606/151, 153, 606/154, 155, 159, 184, 185; 604/167.01, 167.02, 288.01, 164.04, 174; 128/898

(56) References Cited

U.S. PATENT DOCUMENTS

| | | | | | |
|---|---|---|---|---|---|
| 4,624,257 A | * | 11/1986 | Berggren et al. | ............ | 606/153 |
| 4,657,019 A | * | 4/1987 | Walsh et al. | ................. | 606/153 |
| 5,904,697 A | * | 5/1999 | Gifford et al. | ............... | 606/155 |
| 5,944,730 A | * | 8/1999 | Nobles et al. | ............... | 606/151 |
| 6,179,849 B1 | * | 1/2001 | Yencho et al. | ............... | 606/153 |
| 6,248,117 B1 | * | 6/2001 | Blatter | ........................ | 606/153 |
| 6,485,496 B1 | | 11/2002 | Suyker et al. | | |

* cited by examiner

*Primary Examiner*—Julian W. Woo
*Assistant Examiner*—Victor Nguyen
(74) *Attorney, Agent, or Firm*—Brian A. Schar; Cindy A. Lynch

(57) ABSTRACT

A method of performing anastomosis includes securing an access port system to an exterior surface of the target vessel to assist in axial alignment, depth registration, and/or sealing when inserting instruments such as punching instruments and anastomosis instruments into the target vessel.

19 Claims, 8 Drawing Sheets

ACCESS PORT SYSTEM FOR ANASTOMOSIS

FIELD OF THE INVENTION

The invention relates to an anastomosis system, and more particularly, the invention relates to an access port system for a vascular anastomosis procedure.

DESCRIPTION OF THE RELATED ART

Vascular anastomosis is a procedure by which two blood vessels within a patient are surgically joined together. Vascular anastomosis is performed during treatment of a variety of conditions including coronary artery disease, diseases of the great and peripheral vessels, organ transplantation, and trauma. In coronary artery disease (CAD) an occlusion or stenosis in a coronary artery interferes with blood flow to the heart muscle. Treatment of CAD involves the grafting of a vessel in the form of a prosthesis or harvested artery or vein to reroute blood flow around the occlusion and restore adequate blood flow to the heart muscle. This treatment is known as coronary artery bypass grafting (CABG).

In the conventional CABG, a large incision is made in the chest and the sternum is sawed in half to allow access to the heart. In addition, a heart lung machine is used to circulate the patient's blood so that the heart can be stopped and the anastomosis can be performed. In order to minimize the trauma to the patient induced by conventional CABG, less invasive techniques have been developed in which the surgery is performed through small incisions in the patients chest with the aid of visualizing scopes. Less invasive CABG can be performed on a beating or stopped heart and thus may avoid the need for cardiopulmonary bypass.

In both conventional and less invasive CABG procedures, the surgeon has to suture one end of the graft vessel to the coronary artery and the other end of the graft vessel to a blood supplying vein or artery, such as the aorta. The suturing process is a time consuming and difficult procedure requiring a high level of surgical skill. Automated anastomosis systems are being developed to replace the suturing process in which one or more automated connecting members connect a graft vessel and a target vessel without suturing. However, when these automated anastomosis systems are deployed it is often difficult to properly align the graft vessel to the hole which is formed in the target vessel. In addition, there is often a problem of blood loss through the hole in the target vessel after the hole is formed and before the anastomosis procedure is completed. Blood loss may be prevented by clamping off the target vessel. However, clamping is undesirable because it may cause plaque to be dislodged and may cause neurological complications.

Accordingly, it would be desirable to provide an access port system for a sutureless vascular anastomosis device which assists in axial alignment, depth registration, and sealing to prevent blood loss when inserting tools into a target vessel.

SUMMARY OF THE INVENTION

The present invention relates to an access port system for a vascular anastomosis procedure.

In accordance with one aspect of the present invention, a system for performing a vascular anastomosis procedure between a graft vessel and a target vessel includes a sealing element configured to substantially seal to a target vessel, a port connected to the sealing element and configured to allow passage of one or more instruments through the port and into the target vessel when the sealing element is substantially sealed to the exterior surface of the target vessel, a tissue cutter configured to be inserted through the port to form an opening in a side wall of the target vessel, an instrument configured to be inserted through the port to connect a graft vessel to the target vessel, and a seal configured to provide a seal between the port and the tissue cutter, and to provide a seal between the port and the instrument.

In accordance with an additional aspect of the present invention, a method of performing a vascular anastomosis procedure includes: substantially sealing an access port system to a target vessel; inserting a tissue cutter through the access port system, while providing a seal between the access port system and the tissue cutter; forming an opening in a side wall of the target vessel with the tissue cutter; removing the tissue cutter from the access port system; inserting an anastomosis instrument through the access port system, while providing a seal between the access port system and the anastomosis instrument; and performing a vascular anastomosis between a graft vessel and the target vessel with the anastomosis instrument.

In accordance with a further aspect of the present invention, a system for performing a vascular anastomosis procedure between a graft vessel and a target vessel includes an access port configured to provide hemostasis for a side hole in a target vessel for the placement of an anastomosis device without the need to clamp the target vessel.

In accordance with another aspect of the present invention, a method of performing a vascular anastomosis procedure includes the steps of: substantially sealing to a target vessel; inserting a tissue cutter through the access port system; forming an opening in a side wall of the target vessel with the tissue cutter; removing the tissue cutter from the access port system; providing a seal in the access port system to substantially prevent blood loss from the opening in the target vessel; inserting an anastomosis instrument through the access port system; and performing a vascular anastomosis between a graft vessel and the target vessel with the anastomosis instrument.

In accordance with an additional aspect of the present invention, a method of performing a vascular anastomosis procedure includes the steps of: positioning an access port system at a target vessel; inserting a tissue cutter through the access port system, while providing registration of a position of the tissue cutter with the access port system; forming an opening in a side wall of the target vessel with the tissue cutter; removing the tissue cutter from the access port system; inserting an anastomosis instrument through the access port system, while providing registration of a position of the anastomosis instrument with the access port system; and performing vascular anastomosis between a graft vessel and the target vessel with the anastomosis instrument.

BRIEF DESCRIPTION OF THE DRAWING FIGURES

The invention will now be described in greater detail with reference to the preferred embodiments illustrated in the accompanying drawings, in which like elements bear like reference numerals, and wherein.

DETAILED DESCRIPTION OF THE INVENTION

Figure 1:
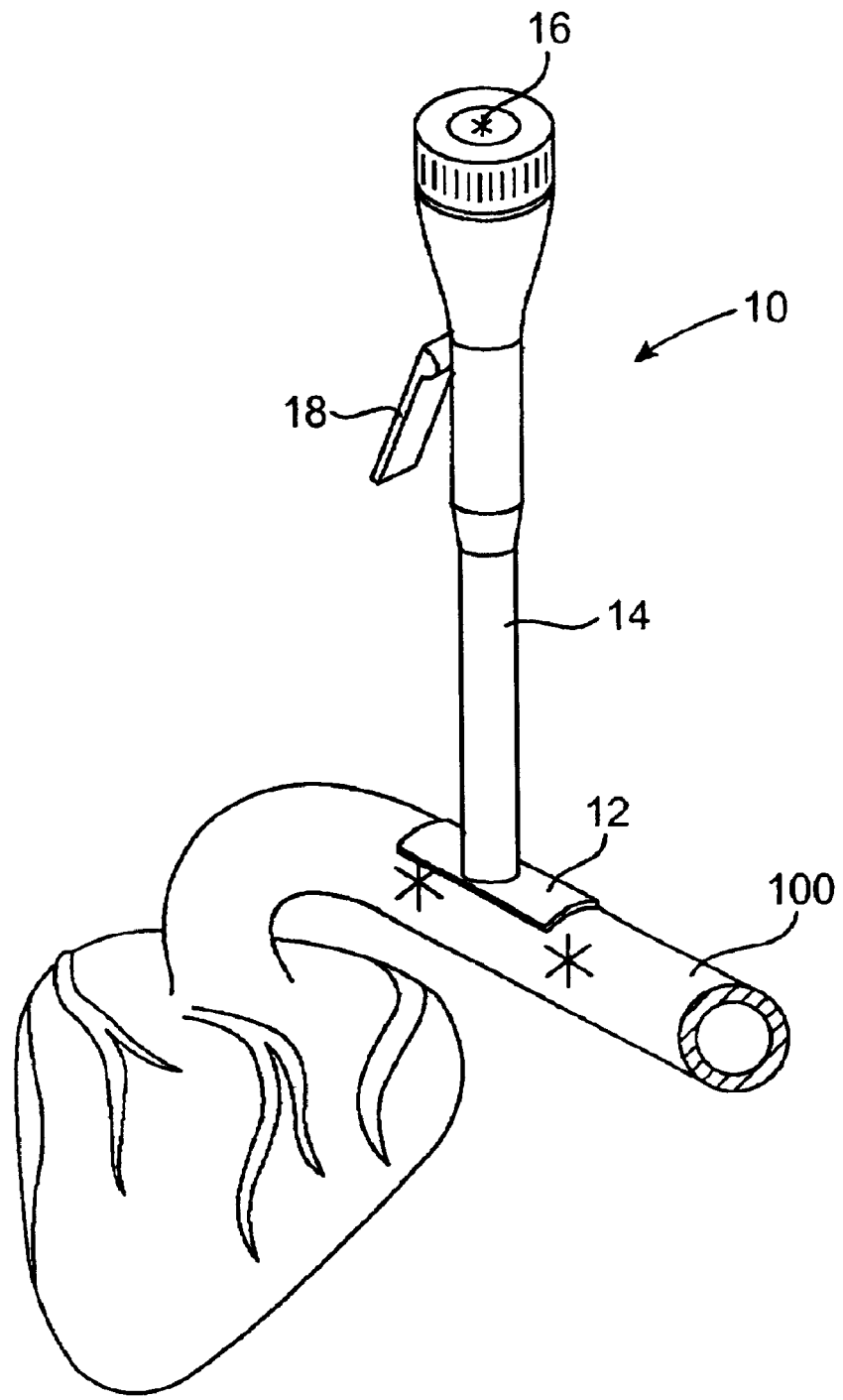
FIG. 1 is a perspective view of an access port system positioned on an aorta for performing a vascular anastomosis procedure.

An access port system 10, as shown in FIG. 1, provides a passageway through which instruments are inserted into a target vessel during performance of an anastomosis procedure. The access port system 10 is apposed to an exterior surface of the target vessel and assists in axial alignment, depth registration, and sealing when inserting instruments into the target vessel. The access port system 10 provides the capability of placing punching instruments, anastomosis instruments, and other instruments in their correct positions relative to a target vessel and providing hemostasis while inserting instruments into and removing instruments from the target vessel. The access port system 10 also provides hemostasis for the placement of an anastomosis device without clamping the target vessel.

The access port system 10 includes a sealing element or sealing plate 12 which is configured to conform to and substantially seal to an exterior wall of a target blood vessel 100, such as the aorta. A port 14 is connected to the sealing plate 12 and is configured to allow passage of instruments through the port and into the target vessel 100. The port 14 is a tubular member which provides axial and longitudinal alignment or registration of instruments inserted into the target vessel 100. A proximal end of the port 14 is provided with a seal 16 in the form of a flapper valve, an elastomeric valve, or other valve. The seal 16 provides hemostasis while moving instruments into and out of the port 14. In particular, the seal 16 prevents blood loss from an opening formed in the target vessel by completely sealing the lumen of the port 14 when no instrument is in use and by sealing around a instrument when the instrument is inserted into the port.

The access port system 10 of FIG. 1 is used in an anastomosis procedure by first locating a position on a target vessel 100 for connection of the graft vessel. The access port system 10 is then held at the desired position and the sealing plate 12 is secured in place against the exterior wall of the target vessel 100. The sealing plate 12 may be secured in place by manually pressing the sealing plate against the target vessel, by suction as will be described below, by a temporary adhesive, or by other known methods.

Once the access port system 10 is positioned on the target vessel, a tissue cutter is inserted through the lumen of the port 14 and forms an opening in the target vessel. The term "tissue cutter," as used herein, is intended to mean any instrument which forms an opening in a target vessel, including tissue punches which cut a plug of tissue and tissue cutters which form an incision. The tissue cutter is then removed and an instrument for performing anastomosis is inserted through the port 14. The anastomosis procedure is then performed.

The instrument for performing anastomosis may be any of the known automated anastomosis systems such as those that use staples, sutures, one piece devices, or multi-piece devices to connect an end of a graft vessel to an opening in a side wall of a target vessel. Examples of anastomosis instruments are described in U.S. Pat. Nos. 6,179,849 and 6,206,913 and in WO 00/69343 and WO 01/08601.

Axial alignment of the instruments with the opening in the target vessel is provided by the port 14. In addition, depth registration of the instruments may be provided by features, such as protrusions within the port 14 or a proximal end of the port. An actuator handle 18 may also be provided to register the tissue cutter and/or other instruments within the port 14.

Once the anastomosis procedure has been completed, the instrument and the access port system 10 are removed from the target vessel leaving the graft vessel connected to the target vessel. The access port system 10 and instrument may be removed together or separately.

Figure 2:
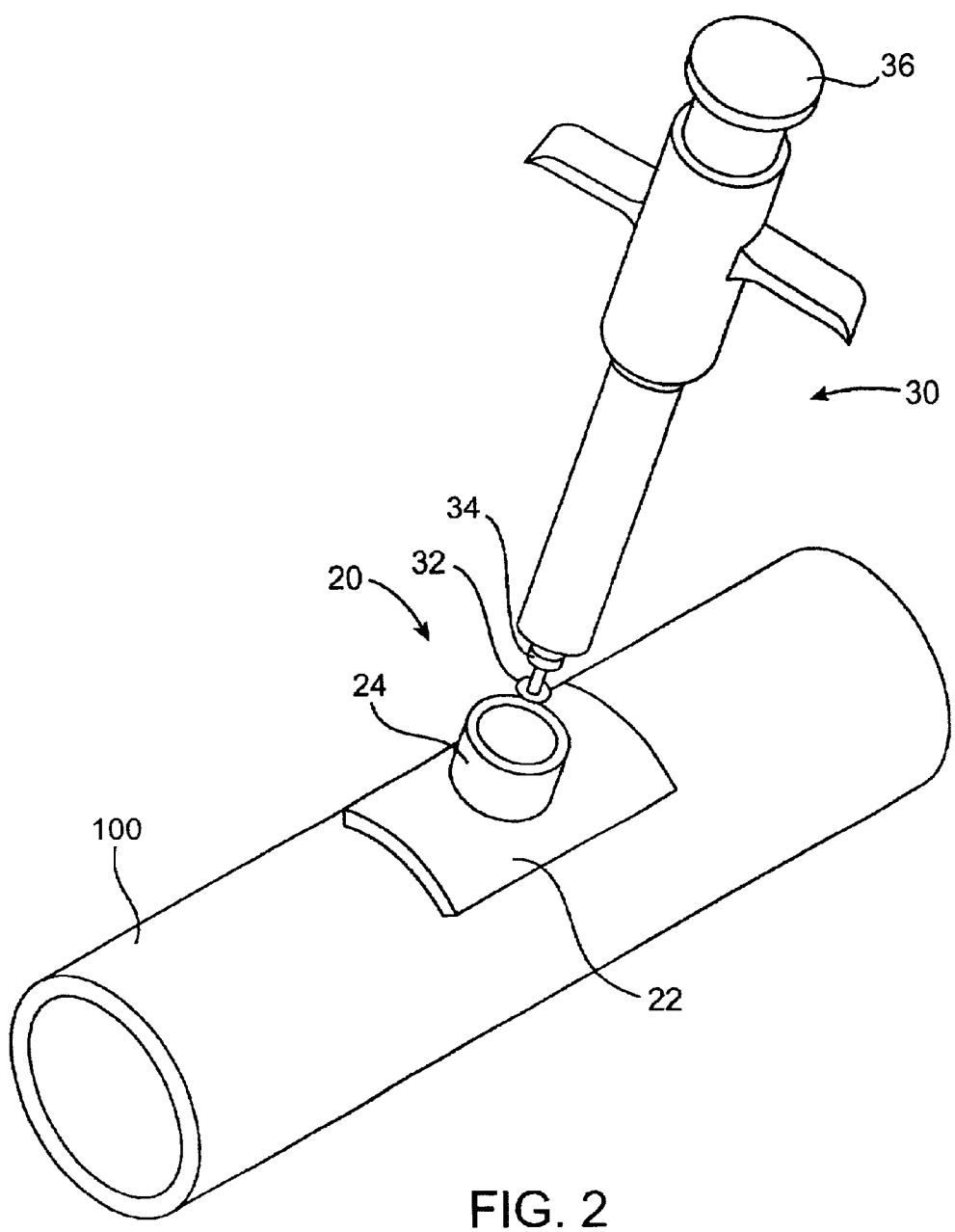
FIG. 2 is a perspective view of an alternative embodiment of an access port system positioned on a blood vessel with a tissue cutter arranged to be inserted through the access port.

FIG. 2 illustrates an alternative embodiment of an access port system 20 having a sealing plate 22 and a port 24 which is shorter than the one shown in FIG. 1. FIG. 2 also shows one exemplary embodiment of a tissue cutter 30 for use with the access port system. The tissue cutter 30 has a conical shaped anvil 32 which penetrates the target vessel wall and an annular cutting edge 34 which moves with respect to the anvil by actuation of the punch handle 36 to remove a plug of tissue. As in the embodiment of FIG. 1, the access port system 20 includes an internal seal (not shown) within the port 24 which prevents blood leakage when no instrument is present in the port and provides a seal around the instruments when present.

Figure 3:
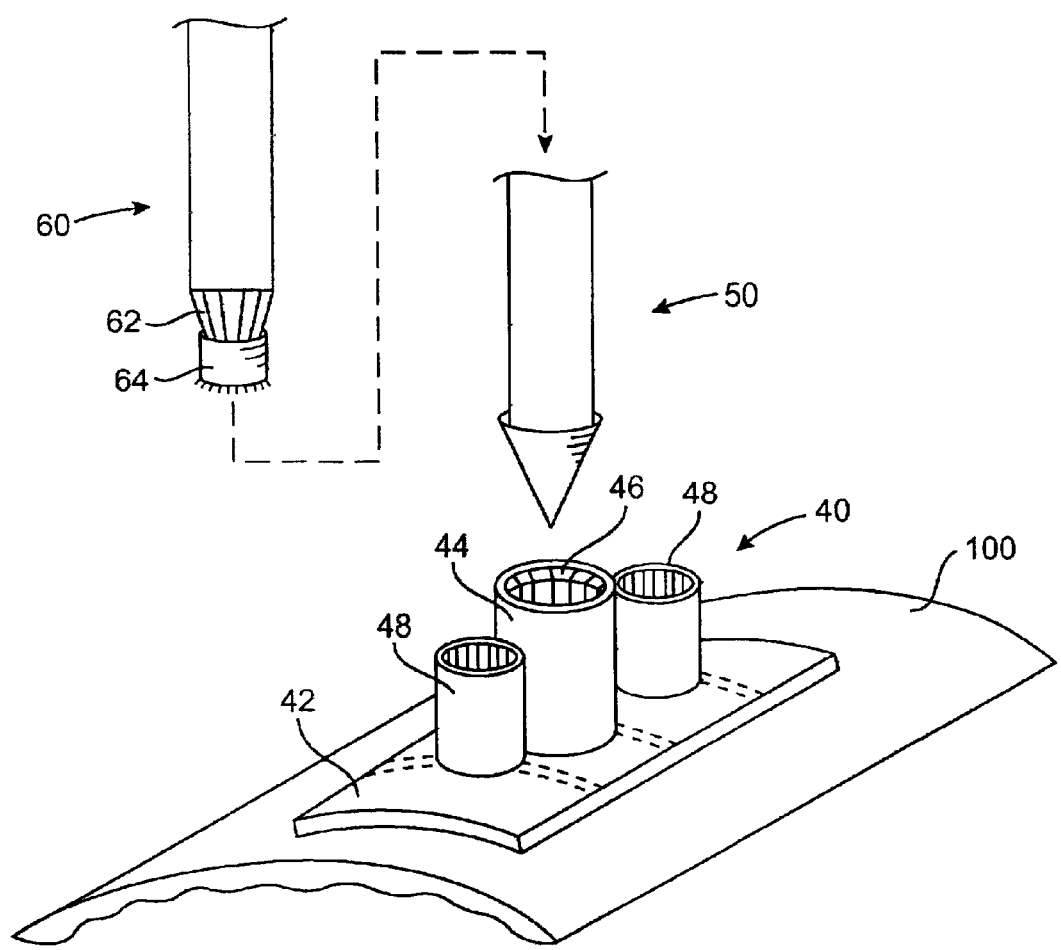
FIG. 3 is an enlarged perspective view of a further alternative embodiment of an access port system with a tissue cutter and an instrument for performing anastomosis.

FIG. 3 illustrates an alternative embodiment of an access port system 40 which includes a sealing plate 42 and a centrally located port 44 having a sealing valve 46. Arranged on opposite sides of the port 44 are two vacuum risers 48 which deliver a suction to seal the sealing plate 42 to the exterior wall of the target vessel 100. The suction risers 48 each have a distal end in fluid communication with a bottom side of the sealing plate 42 and a proximal end configured to receive a suction tube which is connected to a suction source with a variable suction.

Figure 4:
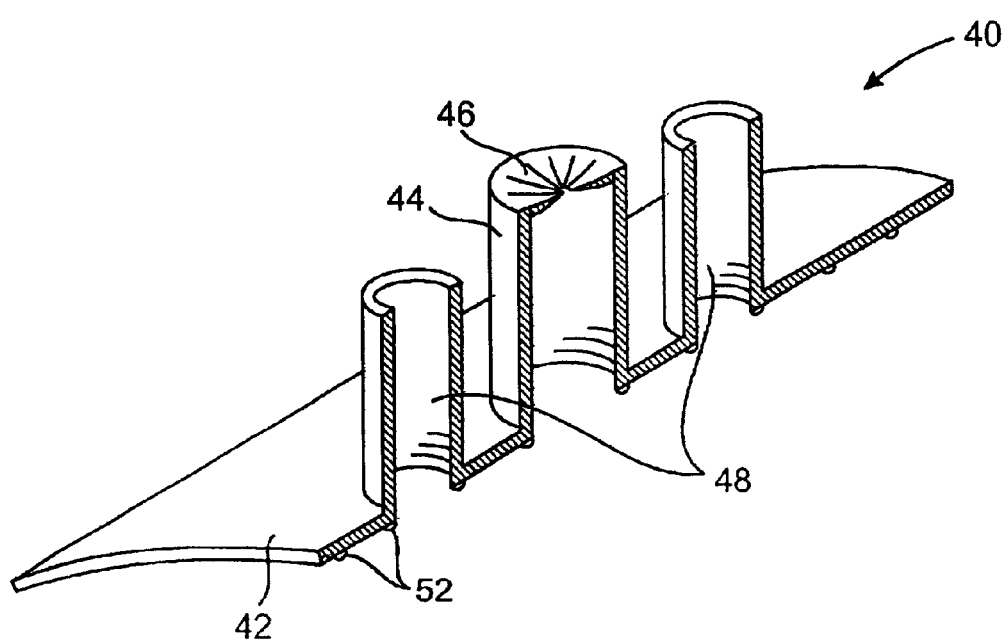
FIG. 4 is a cross sectional perspective view of the access port system of FIG. 3.
Figure 5:
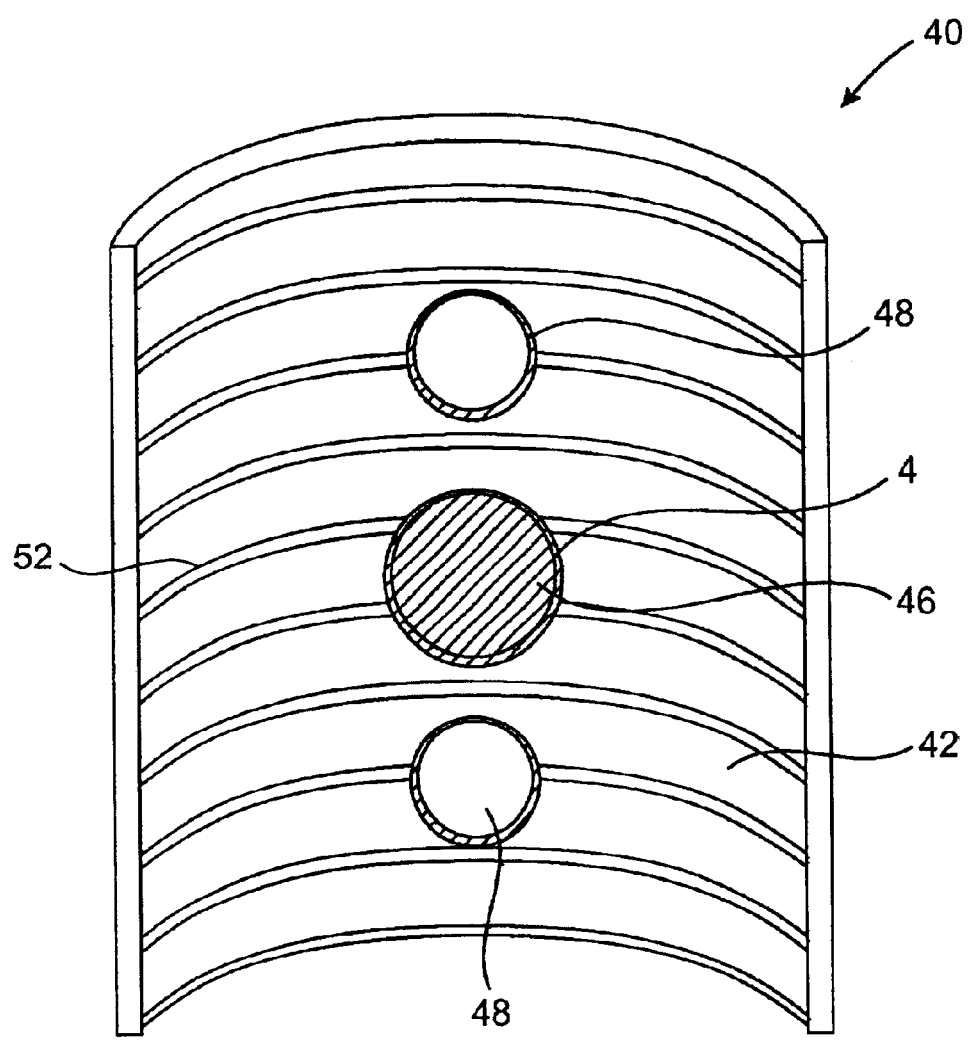
FIG. 5 is a bottom view of the access port system of FIG. 3.

As shown in FIGS. 4 and 5, the sealing plate 42 includes a plurality of sealing ribs 52 on a bottom side or tissue contacting side of the plate. The sealing ribs 52 create channels which assist in suction sealing of the sealing plate 42 to the wall of the blood vessel. Although the ribs 52 illustrated form parallel channels, channels of other shapes may also be created. In addition, although two suction risers 48 have been shown, any number and arrangement of suction risers may be used to secure the sealing plate to the wall of the target vessel 100.

FIG. 3 also shows a schematic illustration of a tissue cutter 50 and an anastomosis instrument 60 with an attached anastomosis device 62 and a graft vessel 64. The tissue cutter 50 and the anastomosis instrument 60 are both configured to be inserted through the port 44 and into the target vessel 100. The tissue cutter 50 and anastomosis instrument 60 are merely schematic representations of the type of instruments which may be used. Other known surgical instruments may also be used with the access port system of the present invention.

The seal 46 illustrated in FIG. 3 is shown in an open position in which the instruments would be received. In a closed position, as shown in FIG. 4, the seal 46 will completely close a lumen of the port 44 preventing blood loss from the anastomosis site. The seal 46 may be an elastomeric seal, flapper valve, or other known seal. The seal 46 is preferably formed of a biocompatible material such as silicone, latex, plastic, nylon, or other material.

Figure 6:
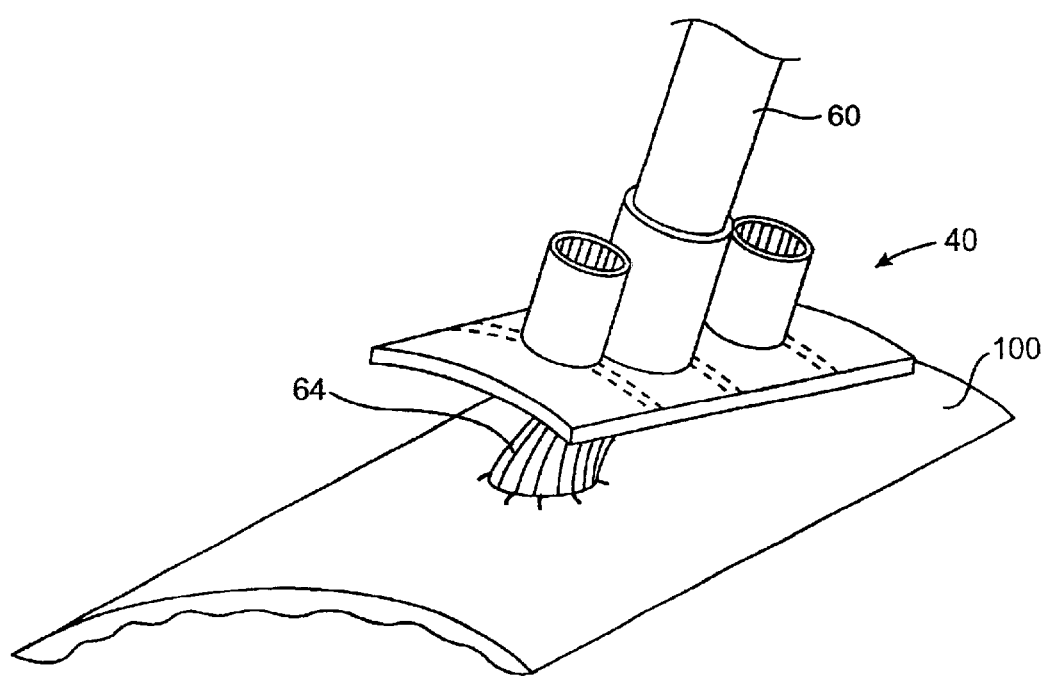
FIG. 6 is a perspective view of the access port system of FIG. 3 once the anastomosis has been performed and the access port system is being removed.

FIG. 6 illustrates the removal of the access port system 40 after the end of a graft vessel 64 has been connected to the target vessel 100. In FIG. 6, the access port system 40 and the anastomosis instrument 60 are being removed simultaneously from the anastomosis site as the graft vessel 64 slides out of the anastomosis instrument.

Figure 7:
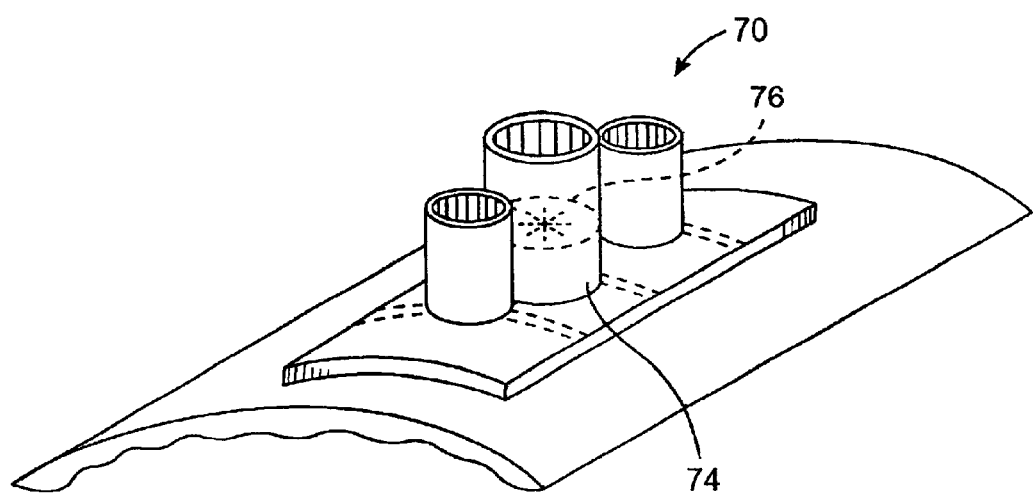
FIG. 7 is a perspective view of another alternative embodiment of an access port system.

FIG. 7 illustrates an alternative embodiment of an access port system 70 in which a hemostasis seal 76 is centrally located within the port 74. It should be understood that the location and configuration of the seal 76 may be varied without departing from the invention.

Figure 8:
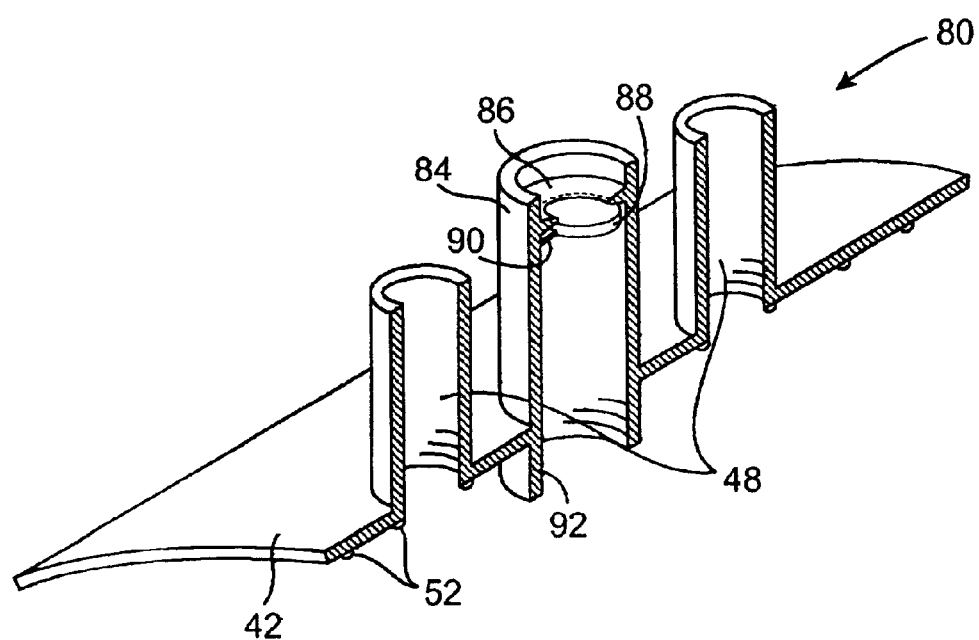
FIG. 8 is a cross sectional perspective view of an alternative embodiment of the access port system of the present invention.

FIG. 8 illustrates an alternative embodiment of an access port system in which the port 84 includes a first seal 86 and a second seal 88. The first seal 86 is in the form of a resilient sealing ring or gasket and provides a seal between the port 84 and the instruments inserted into the port. The second seal 88 is a disk shaped flapper valve which provides hemostasis when instruments are not received in the port 84. The flapper valve 88 seats against the resilient ring 86 in a closed position and is mounted on a resilient hinge 90 which allows the flapper valve to be pushed out of the way by an inserted instrument. The embodiment of FIG. 8 also includes an inwardly extending portion 92 of the port 84 which allows the access port system to provide sealing within an opening formed in the target vessel.

Although the illustrated embodiments of the access port system according to the present invention include a port which is substantially perpendicular to the wall of the blood vessel, it may be desirable to provide a port arranged at a predefined angle with respect to the blood vessel. For example, when forming an anastomosis between a graft vessel and a coronary artery it is desirable to position the graft at an angle so that blood flow from the graft passes into the coronary with minimal turbulence and associate thrombosis.

The access port systems according to the present invention may be used either in open chest or closed chest surgery and on a beating or stopped heart. The access port systems may be used for proximal or distal anastomosis, i.e. connection of a graft vessel to the aorta or coronary artery. The graft vessel may be a natural or synthetic graft, a mammary artery, or other vessel used for performing an anastomosis procedure. Although the invention is particulary designed for use in performing vascular anastomosis it may also be used for other non-vascular anastomosis.

While the invention has been described in detail with reference to the preferred embodiments thereof, it will be apparent to one skilled in the art that various changes and modifications can be made and equivalents employed, without departing from the present invention.

What is claimed is:

1. A method of performing a vascular anastomosis procedure, the method comprising:

substantially sealing an access port system to a target vessel;

inserting a tissue cutter through the access port system, while providing a seal between the access port system and the tissue cutter;

forming an opening in a side wall of the target vessel with the tissue cutter;

removing the tissue cutter from the access port system;

inserting an anastomosis instrument through the access port system, while providing a seal between the access port system and the anastomosis instrument; and performing a vascular anastomosis between a graft vessel and the target vessel with the anastomosis instrument.

2. The method of claim 1, wherein the access port system ensures a desired axial alignment of the tissue cutter and the anastomosis instrument.

3. The method of claim 1, wherein the tissue cutter and anastomosis instrument are inserted to a predetermined depth by registration provided by the access port system.

4. The method of claim 1, further comprising the step of maintaining hemostasis between the steps of removing the tissue cutter and inserting the anastomosis instrument.

5. The method of claim 4, wherein the step of maintaining hemostasis is performed by a seal within the access port system.

6. The method of claim 1, wherein the step of sealing the access port system to an exterior of the target vessel is performed by manual pressure.

7. The method of claim 1, wherein the step of sealing the access port system to an exterior of the target vessel is performed by applying a suction to an exterior wall of the target vessel with the access port system.

8. The method of claim 1, wherein the vascular anastomosis procedure is a closed chest procedure.

9. The method of claim 1, wherein the access port system is sealed to an exterior of the target vessel.

10. The method of claim 1, wherein the access port system is sealed to an interior of the opening in the target vessel.

11. A method of performing a vascular anastomosis procedure, the method comprising:

substantially sealing an access port system to a target vessel;

inserting a tissue cutter through the access port system;

forming an opening in a side wall of the target vessel with the tissue cutter;

removing the tissue cutter from the access port system;

providing a seal in the access port system to substantially prevent blood loss from the opening in the target vessel;

inserting an anastomosis instrument through the access port system; and performing a vascular anastomosis between a graft vessel and the target vessel with the anastomosis instrument.

12. The method of claim 11, wherein the access port system ensures a desired axial alignment of the tissue cutter and the anastomosis instrument.

13. The method of claim 11, wherein the tissue cutter and anastomosis instrument are inserted to a predetermined depth by registration provided by the access port system.

14. The method of claim 11, wherein the step of sealing the access port system to an exterior of the target vessel is performed by manual pressure.

15. The method of claim 11, wherein the step of sealing the access port system to an exterior of the target vessel is performed by applying a suction to an exterior wall of the target vessel with the access port system.

16. A method of performing a vascular anastomosis procedure, the method comprising:

positioning an access port system at a target vessel;

inserting a tissue cutter through the access port system, while providing registration of a position of the tissue cutter with the access port system;

forming an opening in a side wall of the target vessel with the tissue cutter;

removing the tissue cutter from the access port system;

inserting an anastomosis instrument through the access port system, while providing registration of a position of the anastomosis instrument with the access port system; and preforming vascular anastomosis between a graft vessel and the target vessel with the anastomosis instrument.

17. The method of claim 16, wherein the access port system provides depth registration for the tissue cutter and the anastomosis instrument.

18. The method of claim 16, wherein the access port system provides axial alignment for the tissue cutter and the anastomosis instrument.

19. The method of claim 16, wherein the access port system provides hemostasis for the opening formed in the target vessel.

* * * * *